United States Patent [19]

Cho et al.

[11] Patent Number: 5,747,521
[45] Date of Patent: May 5, 1998

[54] N-CINNAMOYL-2-METHYL-5-METHOXY-3-INDOLEACETIC ACID ESTER, AND PHARMACEUTICAL PREPARATION CONTAINING THE SAME

[75] Inventors: Eui Hwan Cho; Sun Gan Chung, both of Seoul; Kyou Heung Lee; Si Kyung Park, both of Kyungki-do, all of Rep. of Korea

[73] Assignee: Samjin Pharm. Co., Ltd., Seoul, Rep. of Korea

[21] Appl. No.: 403,794

[22] PCT Filed: May 6, 1993

[86] PCT No.: PCT/KR93/00038

§ 371 Date: May 4, 1995

§ 102(e) Date: May 4, 1995

[87] PCT Pub. No.: WO94/06769

PCT Pub. Date: Mar. 3, 1994

[30] Foreign Application Priority Data

Sep. 16, 1992 [KR] Rep. of Korea ............... 92-16823

[51] Int. Cl.$^6$ .................. A61K 31/405; C07D 405/12; C07D 209/26
[52] U.S. Cl. ............................... 514/420; 548/500
[58] Field of Search ........................... 548/500; 514/420

[56] References Cited

U.S. PATENT DOCUMENTS

| | | | |
|---|---|---|---|
| 3,679,672 | 7/1972 | Yamamoto et al. | 548/500 |
| 4,165,428 | 8/1979 | Noda et al. | 548/500 |
| 4,181,740 | 1/1980 | Tricerri Zumin et al. | 548/500 |

FOREIGN PATENT DOCUMENTS 4-275271  9/1992  Japan ..................... 548/500

OTHER PUBLICATIONS

Cram & Hammond, "Organic Chemistry", McGraw-Hill Book Co NY., 2nd Edition, pp. 565–567, 1964.
Ghyczy et al, "Injectable pharmaceutical, etc " CA 94: 36367 e (1981).
Khanna, "Oral retard or repeat drug, etc " CA 115:35728p (1991).
Yuan et al, "Pharmacological actions, etc " CA 105:202902t (1986).

Primary Examiner—Patricia L. Morris
Attorney, Agent, or Firm—Birch, Stewart, Kolasch & Birch, LLP

[57] ABSTRACT

The present invention relates to a new N-cinnamoyl-2-methyl-5-methoxy-3-indoleacetic ester represented by the following general formula (I). It is manufactured by causing N-cinnamoyl-2-methyl-5-methoxy-3-indoleacetic acid represented by the following general formula (II) or a reactive derivative thereof to react with a compound represented by the following general formula (III)

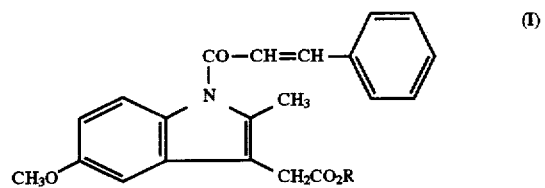

(I)

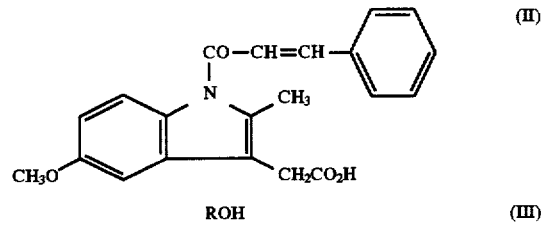

(II)

ROH     (III)

wherein, R is $-CH_2CH=CH-CH_2OH$,

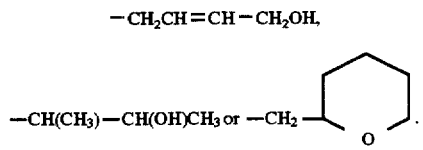

The inventive compounds are effective to the same extent as the existing cinmetacin, and are also excellent in greatly reducing fatal side effects like a gastric ulcer, that are associated with cinmetacin or an intestinal ulcer.

2 Claims, No Drawings

N-CINNAMOYL-2-METHYL-5-METHOXY-3-INDOLEACETIC ACID ESTER, AND PHARMACEUTICAL PREPARATION CONTAINING THE SAME

DETAILED DESCRIPTION OF THE INVENTION

The present invention relates to a new N-cinnamoyl-2-methyl-5-methoxy-3-indoleacetic acid ester represented by the following general formula (I)

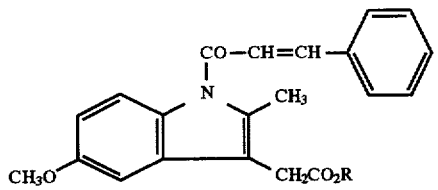

wherein, R is $-CH_2CH=CH-CH_2OH$, $-CH(CH_3)-CH(OH)CH_3$ or

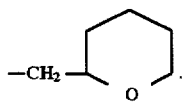

The N-cinnamoyl-2-methyl-5-methoxy-3-indoleacetic acid represented by the following general formula (II) is generally called cinmetacin and now used as an anti-inflammatory and analgesic agent.

However, the anti-inflammatory and analgesic agents which are affiliated with indoleacetic acid like indomethacin and cinmetacin involve a problem by causing a gastric ulcer and are restricted in their use owing to such an adverse reaction thereof.

Consequently, earnest study is given at a continued pace to reducing gastrointestinal trouble caused by such anti-inflammatory and analgesic agent.

As a result of researches conducted for a long time to solve a problem posed by the indoleacetic acid, the present invention is brought to completion by developing a compound represented by the above general formula (I) which makes little difference from cinmetacin in efficacy and alleviates gastrointestinal trouble substantially.

It is therefore an abject of the present invention to provide a compound represented by the above general formula (I).

Another object of the present invention is to provide a method of manufacturing the compound represented by the above general formula (I).

Still another object of the present invention is to provide a pharmaceutical preparation which contains the compound represented by the above general formula (I) as an effective component.

The invented compound represented by the formula (I) is manufactured by causing N-cinnamoyl-2-methyl-5-methoxy-3-indoleacetic acid or its reactive derivative to react upon a compound represented by the following general formula (III). When represented by a reaction formula, it is as follows

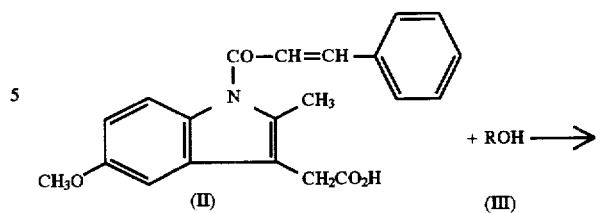

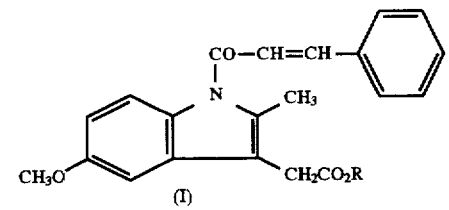

wherein, R is $-CH_2CH=CH-CH_2OH$, $-CH(CH_3)-CH(OH)CH_3$ or

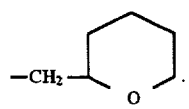

The synthetic reaction formulas of the invented compounds 1, 2, 3 are as follows:

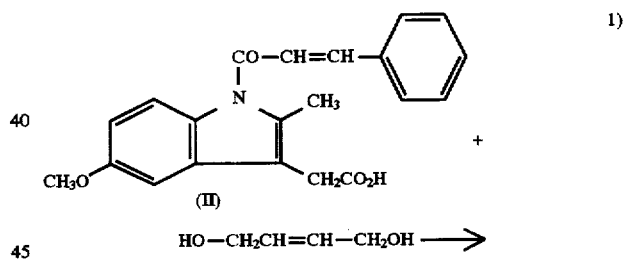

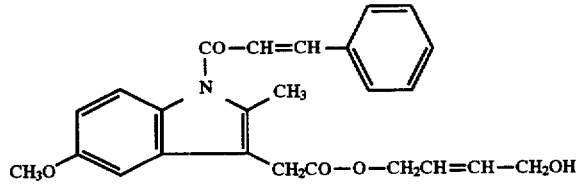

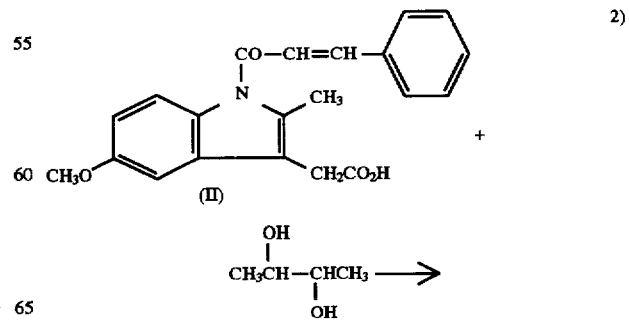

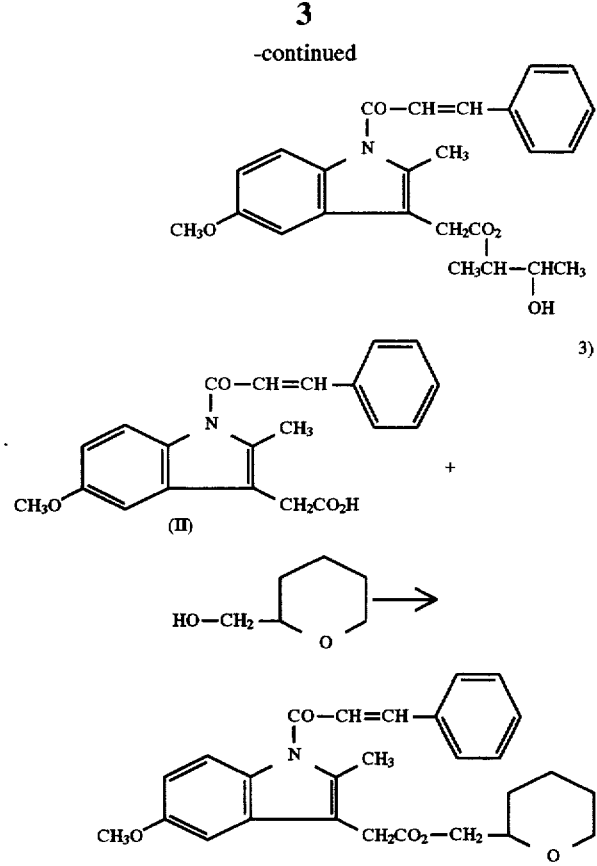

In the above reaction schemes 1-3, reactive derivatives of cinmetacin can be used.

As the reactive derivatives of cinmetacin, an acid salt, an acid anhydride, a mixed acid anhydride, an active ester and an active amide can be taken as examples.

The acid salt includes a usual acid halide like an acid chloride, an acid bromide and an acid iodide.

As the acid anhydride, an anhydride with a lower fatty acid like an acetic anhydride can be taken as an examples.

As the active amide, an amide with hydroxybenzotriazole can be taken as an example.

Regarding a reaction in the present invention, it is desirable to produce it in usual inactive organic solvents with exert no influence thereon, such as a lower ether like dimethyl ether and diethyl ether, a cyclic ether like tetrahydrofuran and dioxane, an aromatic hydrocarbon like benzene, toluene and xylene, a halogenated hydrocarbon like chloroform and methylene chloride.

In the case where reaction is produced with a compound represented by the formula (II), it can be produced in the presence of a usual condensing agent like cyclohexylcarbodiimide.

In the case where reaction is produced with a reactive derivative of a compound represented by the formula (II) like a acid halide thereof, it is desirable to produce it in the presence of a hydroxide of alkali metals or alkaline earth metals, or a inorganic base like a carbonate and a bicarbonate, or aliphatic or aromatic organic amine like trimethyl amine, triethyl amine and pyridine as a acid receptor in order to remove halogenated hydrogen which rises as a by-product.

It is desirable to produce reaction at 10° to 100° C. or preferably at the temperature below the boiling point of a solvent to be used.

After reaction, it is treated by taking advantage of neutralization, extraction, washing, desiccation and concentration which are usually used in synthetic chemistry and, if necessary, purification by chromatography.

The invented compound takes effect to the same extent as the existing cinmetacin, and moreover, it is a compound excellent in greatly reducing a fatal side effect like a gastric ulcer or an intestinal ulcer.

The invented compound can be administered in the form of a usually manufactured drug like a tablet, a capsule, a syrup, a solution, an injection, a cataplasma and an ointment which are usually used pharmaceutically together with excipients or auxiliaries which are usually used pharmaceutically.

The invented compound can be different in the amount used according to the condition, age and sex of a patient, but 50 to 2,000 mg can be adminstered once or several times a day.

The invented compound can also be administered in combination with other effective medicines.

The present invention will now be described in detail with examples. The temperature referred to in the present specification and examples is the centigrade temperature.

EXAMPLE 1

Synthesis of 0-(4-hydroxy-2-butene)-N-cinnamoyl-5-methoxy-2-methyl-3-indoleacetate (Compound 1)

Cinmethacin chloride is manufactured by dissolving 28 g of cinmetacin in 500 ml of benzene, adding thereto 22 ml of oxalyl chloride and refluxing it for 3 hours and then evaporating a dissolvent. The obtained cinmetacin chloride is dissolved in 300 ml of tetrahydrofuran and 12.8 ml of 1,4-butenediol is added thereto in drops. After 11 ml of pyridine is put therein, a formed deposit is removed and a solution is left alone for one day. Then pyridine is completely removed by concentrating the solution. The concentrated solution is dissolved in chlroroform and adjusted to pH 2 with 10% hydrochloric acid. Then it is extracted with chloroform three times repeated and the extracted solutions are concentrated by putting them together. A product obtained by purifying the concentrated solution by silica-gel column chromatography (ether/hexane =10/1) is re-crystallized with ether/hexane and 25 g of pale yellow crystal (yield: 89%, melting point 75–76 degrees) is thereby obtained.

$^1$H-NMR(CDCl$_3$, TMS, ppm):

2.58(3H,s,—CH$_3$), 3.67(2H,s,—CH$_2$—), 3.84(3H,s,—OCH$_3$), 4.19(2H,d,—CH$_2$—), 4.68(2H,d,—CH$_2$—), 5.71(2H,m,—CH=CH—), 6.77—8.0(10H,m)

IR(KBr, cm$^{-1}$) :

3300(0—H), 2920(C—H), 1730(C=O), 1680(C=O), 1620(C=C), 1480(C=C), 1090(C—0)

EXAMPLE 2

Synthesis of 0-(3-hydroxy-2-buthanyl)-cinnamoyl-5-methoxy-2-methyl-3-indoleacetate (Compound 2)

28 g of cinmetacin is dissolved in benzene and 22 ml of oxalyl chloride is added thereto. Then it is refluxed for 3 hours and a dissolvent evaporated. Cinmethacin chloride obtained in this way is dissolved in 300 ml of tetrahydrofuran and 6.6 ml of 2,3-dihydroxy buthane is added thereto in drops. A deposit formed after 11 ml of pyridine is put therein is removed by filtration and the remaining pyridine is completely removed by concentrating a solution left alone for one day. The concentrated solution is dissolved in chloroform and adjusted to pH 2 with 10% hydrochloric acid and then extracted with chloroform three times. A dissolvent is removed by concentrating the extracted solutions put together. The concentrated solution thereby obtained is purified by silica-gel column chromatography (ether/hexane=10/1). A product thereby obtained is re-crystallized with ether/hexane and 22 g of pale yellow crystal (yield: 78%, melting point 74–77 degrees) is thereby obtained.

$^1$H-NMR(CDCl$_3$, TMS, ppm):

1.04–1.26(6H,m), 2.60(3H,s,—CH$_3$), 3.47(1H,s,—O—CH) 3.68(2H,m,—CH$_2$—), 3.85(3H,s,—OCH$_3$), 6.78–8.0(10H,m)

IR(KBr, cm$^{-1}$): 3450(O—H), 2950(C—H), 1690(C=O), 1680(C=O), 1610(C=C), 1480(C=C), 1230(C—C), 1090(C—O)

EXAMPLE 3

Synthesis of O-(2-tetrahydropyranil methyl)-N-cinnamoyl-5-methoxy-2methyl-3-indoleacetate (Compound 3) 28 g of cinmetacin is dissolved in 500 ml of benzene and 22 ml of oxalyl chloride is added thereto. After it is refluxed for 3 hours, a dissolvent evaporated. Cinmethacin chloride obtained by doing so is dissolved in 300 ml of tetrahydrofuran. After 4.5 ml of tetrahydropyran-2-methanol is put therein and 9 ml of pyridine is added thereto in drops, it is agitated. After a formed deposit is removed by filtration and a solution is left alone for one day, pyridine is completely removed by concentrating the solution. The concentrated solution is purified by silica-gel chromatography (ether/hexane=10/1) and a product thereby obtained is made into 24 g of pale yellow crystal (yield: 85%, melting point 97–99 degrees) by re-crystallization thereof with ethanol.

$^1$H-NMR(CDCl$_3$, TMS, ppm):

1.44–1.57(6H,m), 2.61(3H,s,—CH$_3$), 3.72(2H,s,—CH$_2$—), 3.87(3H,s,—OCH$_3$), 4.05–4.13(5H,m), 6.0–7.77(10H,m)

IR(KBr, cm$^{-1}$):

2930(C—H), 2830(C—H), 1720(C=O), 1660(C=O), 1600(C=C), 1480(C=C), 1230(C—O), 1080(C—O)

EXAMPLE 4

Synthesis of O-(4-hydroxy-2-butene)-N-cinnamoyl-5-methoxy-2-methyl-3indoleacetate (Compound 1)

28 g of cinmetacin is dissolved in 500 ml of benzene and equivalent of dicyclohexyl carbodilmide is added thereto. To it 12.8 ml of 1,4-butenediol is added and agitated for 3 hours under reflux. After a formed deposit is removed by filtration, a great portion of dissolvent is removed by concentration. Then the concentrated solution thereby obtained is dissolved in chloroform and adjusted to pH 2 with 10% hydrochloric acid and extracted three times with chloroform. The extracted solutions are put together and concentrated. The concentrated solution thereby obtained is purified by column chromatography (ether/hexane=10/1) and a product thereby obtained is made into a pale yellow crystal by recrystallization thereof with ether/hexane.

The physical properties of a product obtained by doing so were the same as those obtained in Example 1.

EXPERIMENTAL EXAMPLE 1: Acute toxicity test

In order to get 50% lethal dose (LD$_{50}$) in mice after they are dosed one time, a solution of a drug was administered through the oral or into the abdominal cavity of a group of 10 mature ICR-male mice (weight 20±2 g) performing a fast from the evening before the test and the presence of abnormality in action was observed. The amount of LD$_{50}$ was calculated according to the method of Ritchfield J. T. and Wilcoxon F. (J. Pharmacol., 96, 99–113, 1949) from mortality rate up to 72 hours. Results obtained are the same as shown in Table 1.

TABLE 1

| | Acute toxicity test data | | | | |
|---|---|---|---|---|---|
| Compound | Cinmetacin | Sulindac | Compound 1 | Compound 2 | Compound 3 |
| LD$_{50}$ | | | | | |
| Oral administration (mg/kg) | 820 | 980 | 2000 | 4200 | 6000 |
| Abdominal adminstration (mg/kg) | 495 | 235 | 520 | 570 | 1150 |

As can be seen from the above Table 1, the invented compound is much lower in acute toxicity than the widely known compound.

EXPERIMENTAL EXAMPLE 2: Anti-inflammatory activity test

The carrageenan induced hind-paw edema method according to the Winter method (Proc. Soc. Exp. Biol. Med., 111, 544, 1962) was used. The volume of legs was measured before a solution of a drug was administered to a group of 8 mature male rats (weight 170±20 g) and 0.1 ml /rat of 1% carrageenan physiological saline solution was injected subcutaneously into the sole of hind of leg of rats one hour after the oral administration and edema thereby caused was measured 3 hours and 5 hours thereafter. In this way, a rate of edema formation and a rate of inhibition were calculated. Results obtained are the same as shown in Table 2.

TABLE 2

Anti-inflammatory activity data

| Compound | Amount administered p.o. (mg/kg) | A rate of inhibition (%) | Significance (p.v.) |
|---|---|---|---|
| Cinmetacin | 100 | 65 | 0.01 |
| Compound 1 | 100 | 57 | 0.01 |
| Compound 2 | 100 | 52 | 0.01 |
| Compound 3 | 100 | 43 | 0.01 |

As ascertained in the above Table 2, the invented compounds 1, 2 produced an edema inhibition effect almost similar to the widely known cinmetacin and the compound 3 presented a significant anti-inflammatory action.

EXPERIMENTAL EXAMPLE 3: Analgesic activity test

According to the anti-writhing method by Whittle (Brit. J. Pharmacol., 22, 246, 1964), a solution of a drug was administered through the mouths of a group of 10 mature male ICR-mice (weight 20±2 g) performing a fast for one day. After the lapse of 60 minutes, the number of stretchings in the course of 10 minutes was measured as an index to a algesic sense. Anti-writhing effect was found with a inhibition rate of the drug-administered group for the number of rising of a control group and 507% effective amount($ED_{50}$) was calculated from the inhibition rate according to the Ritchfield and Wilcoxon method (J. Pharmacol., 96, 99, 1949). Results obtained are the same as shown in Table 3.

TABLE 3

Analgesic activity data

| | Cinmetacin | Sulindac | Compound 1 | Compound 2 | Compound 3 |
|---|---|---|---|---|---|
| $ED_{50}$ Oral administration (mg/kg) | 36.0 | 60.0 | 70.0 | 31.0 | 95.0 |

As ascertained in the above Table 3, the invented compound 2 showed analgesic activity equal to cinmetacin and the compounds 1, 3 presented a significant analgesic action.

EXPERIMENTAL EXAMPLE 4: Gastrointestinal trouble test

A solution of a drug was administered through the mouths of a group of 8 mature male SD-rats (weight 130±20 g) performing a fast for 24 hours. 4 hours thereafter, the inside of the stomach was observed with a microscope. Capacity which causes 50% bleeding ($UD_{50}$) was calculated according to the Ritchfield and Wilcoxon method (J. Pahrmacol., 69, 99, 1949) with bleeding more than 1 mm in diameter as positivity. Results obtained are the same as shown in Table 4.

TABLE 4

Gastrointestinal trouble test data

| $UD_{50}$\Compound | Cinmetacin | Sulindac | Compound 1 | Compound 2 | Compound 3 |
|---|---|---|---|---|---|
| Oral administration (mg/kg) | 18.0 | 14.0 | 100.0 | 175.0 | 230.0 |

As shown in the above Table 4, the invented compounds cause about 50% of laboratory animals to form an ulcer or to bleed within the maximum range of 100–230 mg/kg a time. It is 5 to 13 times as much as cinmetacin. Therefore the invented compounds were proved excellent in greatly reducing gastrointestinal trouble, the main side effect caused by cinmetacin.

Example of preparation 1: Tablets

| | |
|---|---|
| Compound of Example 1 | 100 mg |
| Corn starch | 50 mg |
| Lactose | 50 mg |
| Sodium starch - glycolate | 40 mg |
| H.P.C(Hydroxypropyl cellulose) | 5 mg |
| Magnesium stearate | 5 mg |

A tablet is manufactured by striking the above components into a 50 mg-tablet according to the usual tablet manufacturing method.

| Example of preparation 1: Capsules | |
|---|---|
| Compound of Example 2 | 100 mg |
| Lactose | 50 mg |
| Calcium phosphate, basic | 100 mg |
| H.P.C | 5 mg |
| Magnesium stearate | 15 mg |

A capsule is manufactured by filling up the above components in a hard capsule according to the usual capsule manufacturing method.

What is claimed is

1. A compound represented by the following formula

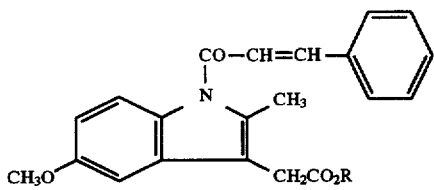

wherein R is

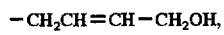

—CH(CH$_3$)—CH(OH)CH$_3$ or —CH$_2$— 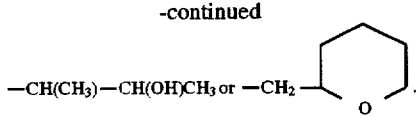.

2. A pharmaceutical composition, which comprises: an effective amount of a compound represented by the following formula (I) together with a pharmaceutically acceptable excipient or auxiliary,

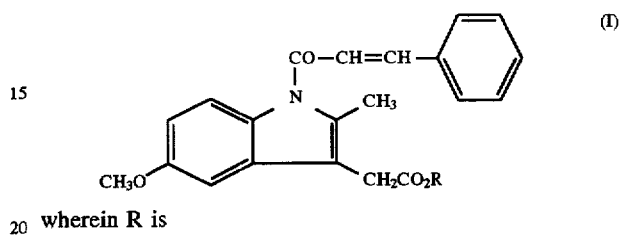 (I)

wherein R is

—CH$_2$CH=CH—CH$_2$OH, —CH(CH$_3$)—CH(OH)CH$_3$ or

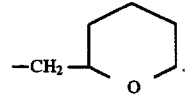.

* * * * *